(12) United States Patent
Shintani et al.

(10) Patent No.: US 8,809,916 B2
(45) Date of Patent: Aug. 19, 2014

(54) PH SENSOR, PH MEASUREMENT METHOD, ION SENSOR, AND ION CONCENTRATION MEASUREMENT METHOD

(75) Inventors: Yukihiro Shintani, Tokyo (JP); Kazuma Takenaka, Tokyo (JP)

(73) Assignee: Yokogawa Electric Corporation, Tokyo (JP)

( * ) Notice: Subject to any disclaimer, the term of this patent is extended or adjusted under 35 U.S.C. 154(b) by 157 days.

(21) Appl. No.: 13/368,563

(22) Filed: Feb. 8, 2012

(65) Prior Publication Data

US 2012/0199884 A1 Aug. 9, 2012

(30) Foreign Application Priority Data

Feb. 9, 2011 (JP) ................................. 2011-026194
Feb. 16, 2011 (JP) ................................. 2011-031102

(51) Int. Cl.
*G01N 27/403* (2006.01)
*G01N 27/414* (2006.01)

(52) U.S. Cl.
CPC .................................... *G01N 27/414* (2013.01)
USPC .................. 257/253; 257/414; 257/E21.005; 257/E21.264; 257/E21.095; 438/14; 438/105; 438/48; 438/49

(58) Field of Classification Search
None
See application file for complete search history.

(56) References Cited

U.S. PATENT DOCUMENTS 5,536,953 A * 7/1996 Dreifus et al. .................. 257/77
7,339,212 B2 3/2008 Kawarada
2009/0278556 A1 11/2009 Man et al.

FOREIGN PATENT DOCUMENTS

| JP | 61-270653 A | 11/1986 |
| JP | 09-005290 A | 1/1997 |
| JP | 2001-242134 A | 9/2001 |
| JP | 2004-109020 A | 4/2004 |
| JP | 2006-275788 A | 10/2006 |
| JP | 2007-078373 A | 3/2007 |
| JP | 2009-236687 A | 10/2009 |

OTHER PUBLICATIONS

H. Kawarada, Y. Araki, T. Sakai, T. Ogawa, and H. Umezawa, Electrolyte-Solution-Gate FETs Using Diamond Surface for Biocompatible Ion Sensors, Mar. 2001,No. 1, p. 79-83.*
Yuan-Lung Chin, Jung-Chuan Choub, Tai-Ping Sun, Wen-Yaw Chung, Shen-Kan Hsiung, A novel pH sensitive ISFET with on chip temperature sensing using CMOS standard process, vol. 76, Issues 1-3, Jun. 1, 2001, pp. 582-593.*
Extended European Search Report dated Jul. 4, 2012, issued in corresponding European Patent Application No. 12154488.6 (11 pages).
Rezek et al., "Intrinsic hydrogen-terminated diamond as ion-sensitive field effect transistor", Sensors and Actuators B: Chemical, vol. 122, No. 2, (Mar. 15, 2007), pp. 596-599, XP005924563.
Kawarada et al., "Electrolyte-Solution-Gate FETs Using Diamond Surface for Biocompatible Ion Sensors", Phys. Stat. Sol. (A) vol. 185, No. 1, (Jan. 1, 2001), pp. 79-83, XP55029183.

(Continued)

*Primary Examiner* — Steven Loke
*Assistant Examiner* — Cuong B Nguyen
(74) *Attorney, Agent, or Firm* — Westerman, Hattori, Daniels & Adrian, LLP

(57) ABSTRACT

A pH sensor may include a reference electrode including a p-channel field effect transistor (FET) whose gate includes a diamond surface having a hydrogen ion insensitive terminal, and a working electrode.

9 Claims, 11 Drawing Sheets

(56) References Cited

OTHER PUBLICATIONS

Chin Y-L et al., "A novel pH sensitive ISFET with on chip temperature sensing using CMOS standard process", Sensors and Actuators B:Chemical, vol. 76, No. 1-3, (Jun. 1, 2001), pp. 582-593, XP004241177.

Denisenko et al., "pH sensing by surface-doped diamond and effect of the diamond surfce termination", Diamond and Related Materials vol. 10, (Jan. 1, 2001), pp. 667-672, XP55029182.

Garrido Jose et al., "pH sensors based on hydrogenated diamond surfaces", Applied Physics Letters, vol. 86, No. 7, (Feb. 9, 2005), pp. 73504-1-073504-3, XP012066402.

Arkadiy Morgenshtein et al., "Design and methodology of ISFET (Ion Sensitive Field Effect Transistor", microsystems for bio-telemetry, (203-04-01), XP55029573.

Hideyuki Watanabe et al., "High-quality homoepitaxial diamond film growth", New Diamond and Frontier Carbon Technology, vol. 12, No. 6, 1 p., (Jan. 1, 2002), XP55029871.

* cited by examiner

AS-GROWN DIAMOND

HYDROGEN TERMINATION

PARTIAL AMINO TERMINATION

PARTIAL FLUORINE TERMINATION

PH SENSOR, PH MEASUREMENT METHOD, ION SENSOR, AND ION CONCENTRATION MEASUREMENT METHOD

BACKGROUND OF THE INVENTION

1. Field of the Invention

The present invention relates to a pH sensor for measuring the pH of a liquid to be measured based on outputs of a reference electrode and a working electrode.

The present invention also relates to ion sensors, particularly a pH sensor among the ion sensors, for measuring an ion concentration of a liquid to be measured based on an output of a reference electrode and an output of a working electrode.

Priority is claimed on Japanese Patent Application No. 2011-026194, filed Feb. 9, 2011, and Japanese Patent Application No. 2011-031102, filed Feb. 16, 2011, the contents of which are incorporated herein by reference.

2. Description of the Related Art

All patents, patent applications, patent publications, scientific articles, and the like, which will hereinafter be cited or identified in the present application, will hereby be incorporated by reference in their entirety in order to describe more fully the state of the art to which the present invention pertains.

A glass electrode type pH sensor is disclosed in Japanese Unexamined Patent Application, First Publication No. 1997 (H09)-005290, in which the pH of a liquid to be measured is measured by detecting a potential difference between the inside and outside of a glass film using a glass electrode that functions as a working electrode. In the pH sensor disclosed in Japanese Unexamined Patent Application, First Publication No. 1997(H09)-005290, a reference electrode is disposed in an internal liquid, such as a potassium chloride solution (KCl solution), that is filled in a holder. Further, a ceramic liquid junction is installed in the holder. When the pH is measured, the glass film and the ceramic liquid junction are dipped into the liquid to be measured. In this case, an internal electrode of a working electrode is electrically connected to an inner wall of the glass film via the internal liquid. On the other hand, the reference electrode is electrically connected to an outer wall of the glass film via the internal liquid, the ceramic liquid junction, and the liquid to be measured. Accordingly, the pH of the liquid to be measured can be measured by detecting a potential difference between the reference electrode and the internal electrode of the working electrode.

In the glass electrode type pH sensor disclosed in Japanese Unexamined Patent Application, First Publication No. 1997 (H09)-005290 or Japanese Unexamined Patent Application, First Publication No. 2007-078373, problems occur such as contamination of the liquid to be measured caused by leakage of the internal liquid, which is contained inside a layer of the holder in which the reference electrode is held, into the liquid to be measured, a change in state caused by moisture vaporization of the internal liquid, crystallization of the internal liquid, and the like.

Further, an ion sensor is disclosed in Japanese Unexamined Patent Application, First Publication No. 2009-236687, which includes first and second ion sensitive field effect transistors (ISFETs), and provides a difference in sensitivity (Nernst response) to measuring-target ions of the two ISFETs.

In the ion sensor disclosed in Japanese Unexamined Patent Application, First Publication No. 2009-236687, a self-assembled monolayer (SAM) is used for ion sensitive and insensitive parts of the ISFET. As such, the SAM has a problem with physical and chemical instability in a high-temperature, high-pressure state of a chemical synthesis plant, or in a strong acid or alkaline process of a semiconductor fabricating process, and thus is difficult to use. Further, in a bioprocess of handling bio-related materials such as proteins, the protein is adsorbed to the SAM, making accurate measurement difficult.

SUMMARY

The present invention provides a pH sensor that resolves the problems of the reference electrode.

The present invention provides an ion sensor that resolves the problems of the reference electrode, and can be used under severe environments.

A pH sensor may include: a reference electrode including a p-channel field effect transistor (FET) whose gate includes a diamond surface having a hydrogen ion insensitive terminal; and a working electrode.

The diamond surface may be formed of as-grown diamond on which hydrogen termination is performed.

The diamond surface may have a content of an $sp^3$ bonded crystal which is more than that of an $sp^2$ bonded crystal.

The diamond surface may include a hydrogen ion insensitive terminal where an oxygen terminal or a fluorine terminal is substituted for part of hydrogen terminals of as-grown diamond on which hydrogen termination is performed.

The working electrode may be a glass electrode.

The working electrode may include an FET whose gate has a hydrogen ion sensitive film.

The pH sensor may further include a temperature sensor that detects a temperature of the FET.

A pH measurement method may include: a step of bringing a liquid to be measured into contact with a reference electrode including a p-channel field effect transistor (FET) whose gate includes a diamond surface having a hydrogen ion insensitive terminal, and a working electrode; and a step of measuring pH of the liquid to be measured based on outputs of the reference electrode and the working electrode.

An ion sensor may include: a reference electrode including a first p-channel field effect transistor (FET) in which a semiconductor surface contains diamond; and a working electrode including a second p-channel FET whose gate portion has a semiconductor surface terminal different from that of a gate portion of the first p-channel FET.

The semiconductor surface of the gate portion of the first p-channel FET may include hydrogen-terminated diamond.

The semiconductor surface of the gate portion of the first p-channel FET may include a hydrogen ion insensitive terminal in which an oxygen terminal or a fluorine terminal is substituted for part of hydrogen terminals of hydrogen-terminated diamond.

The semiconductor surface of the gate portion of the first p-channel FET may have a content of an $sp^3$ bonded crystal which is more than that of an $sp^2$ bonded crystal.

The semiconductor surface of the gate portion of the second p-channel FET may include an ion sensitive terminal in which an amino terminal or an oxygen terminal is substituted for part of hydrogen terminals of hydrogen-terminated diamond.

The ion sensor may further include a temperature sensor that detects a temperature of at least one of the first and second p-channel FETs.

An ion concentration measurement method may include: a step of bringing a liquid to be measured into contact with a reference electrode having a first p-channel FET in which a semiconductor surface includes diamond, and a working electrode including a second p-channel FET whose gate portion has a semiconductor surface terminal different from that of a gate portion of the first p-channel FET; and a step of measuring an ion concentration of the liquid to be measured based on outputs of the reference electrode and the working electrode.

The diamond surface may be formed of hydrogen-terminated conductive diamond.

According to a pH sensor of the present invention, since a reference electrode is formed of a p-channel FET, problems with leakage or time degradation of an internal liquid can be removed from the reference electrode.

According to a pH measurement method of the present invention, since a reference electrode is formed of a p-channel FET, problems with leakage or time degradation of an internal liquid can be removed from the reference electrode.

According to an ion sensor of the present invention, since a semiconductor surface of a first p-channel FET is formed of diamond, it is possible to obtain an ion sensor that can resolve the problems regarding the reference electrode, and can be used under severe environments such high temperature, high pressure, and the like.

According to an ion concentration measurement method of the present invention, since a semiconductor surface of a first p-channel FET is formed of diamond, it is possible to obtain an ion sensor that can resolve the problems regarding the reference electrode, and can be used under severe environments such high temperature, high pressure, and the like.

BRIEF DESCRIPTION OF THE DRAWINGS

The above features and advantages of the present invention will be more apparent from the following description of certain preferred embodiments taken in conjunction with the accompanying drawings, in which.

DETAILED DESCRIPTION OF THE PREFERRED EMBODIMENTS

The present invention will be now described herein with reference to illustrative preferred embodiments. Those skilled in the art will recognize that many alternative preferred embodiments can be accomplished using the teaching of the present invention and that the present invention is not limited to the preferred embodiments illustrated herein for explanatory purposes.

Hereinafter, reference will be made to a pH sensor in accordance with an preferred embodiment of the present invention. The pH sensor in accordance with an preferred embodiment of the present invention is an example in which a reference electrode based on a diamond ion sensitive FET (ISFET) as a p-channel field effect transistor (FET) is combined with a glass electrode in the present invention.

Figure 1:
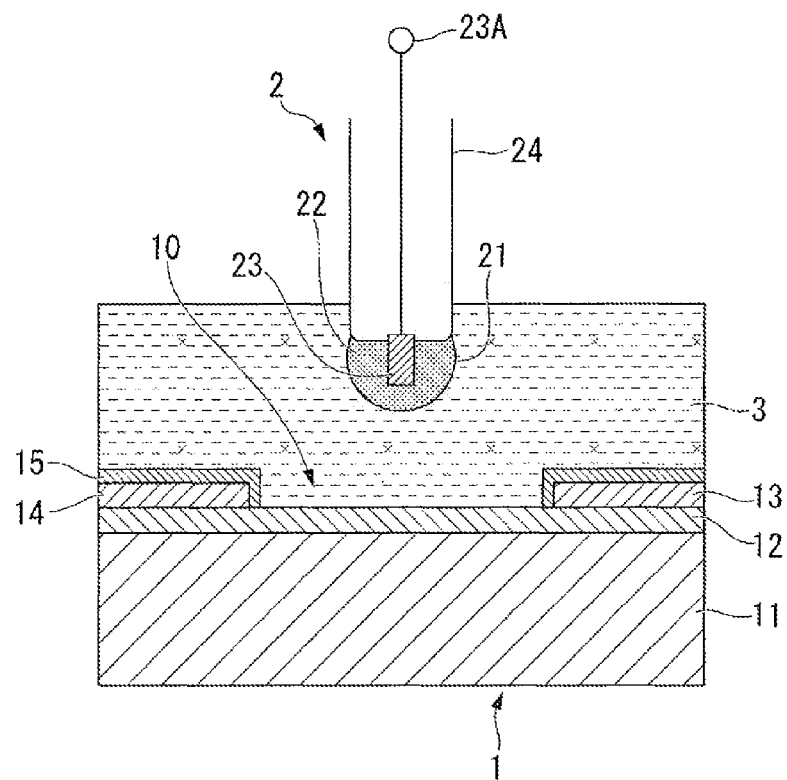
FIG. 1 is a cross-sectional view illustrating the construction of a pH sensor in accordance with a first preferred embodiment of the present invention.
Figure 2:
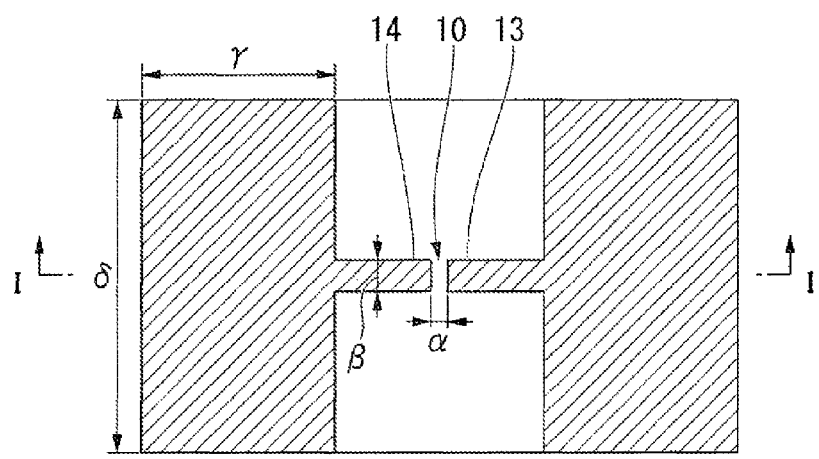
FIG. 2 is a plan view of an ISFET portion of the pH sensor in accordance with the first preferred embodiment of the present invention.

FIG. 1 is a cross-sectional view illustrating the construction of a pH sensor in accordance with a first preferred embodiment of the present invention. FIG. 2 is a plan view of an ISFET portion of the pH sensor in accordance with the first preferred embodiment of the present invention.

A reference electrode 1 includes a silicon wafer 11 on which a diamond thin film 12 is formed, a drain 13 that is formed on the diamond thin film 12, a source 14 that is formed on the diamond thin film 12 so as to be opposite to the drain 13, and a passivation layer 15 that covers the drain 13 and the source 14.

A liquid 3 to be measured is filled between the drain 13 and the source 14. The diamond thin film 12 is in contact with the liquid 3 to be measured. In the pH sensor in accordance with a first preferred embodiment of the present invention, a contact region sandwiched between the drain 13 and the source 14 serves as a gate 10. The drain 13, the source 14, and the gate 10 constitute a p-channel FET. This p-channel FET is an ion sensitive FET (ISFET). This p-channel FET is called a diamond ISFET because it has the diamond thin film 12.

A glass electrode 2 functioning as a working electrode includes a glass film 21 in which an internal liquid 22 (e.g., a potassium chloride solution of pH 7) is filled, an internal electrode 23, such as a silver chloride electrode, that is disposed inside the glass film 21, and a glass support pipe 24 that supports the glass film 21. Further, an output from the internal electrode 23 is transmitted to an output terminal 23A. The glass film 21 and the glass support pipe 24 are in contact with the liquid 3 to be measured. It is shown in FIG. 1 that a width of the glass electrode 2 is less than a distance between the drain 13 and the source 14. However, the width of the glass electrode 2 is generally greater than the distance between the drain 13 and the source 14.

FIG. 2 is a plan view of the ISFET portion constituted of the drain 13, the source 14, and the gate 10 of FIG. 1. The same elements as in FIG. 1 are given the same numerals. The cross-sectional view of FIG. 1 corresponds to a cross section taken along line I-I of the middle portion of FIG. 2.

An arbitrary numerical value may be applied to the size, intervals and the like, of the electrodes of the drain 13 and the source 14. For example, in FIG. 2, a distance a between the drain 13 and the source 14 may be 10 to 1000 μm, a width β of the ISFET portion of the source 14 (or a width of the ISFET portion of the drain 13) may be 0.01 to 50 mm, a length γ of the source 14 (or a length of the drain 13) may be 5 to 50 mm, and a width δ of the source 14 (or a width of the drain 13) may be 5 to 100 mm.

Next, an operation of the pH sensor in accordance with the first preferred embodiment of the present invention will be described.

As shown in FIG. 1, when pH is measured, the liquid 3 to be measured is in contact with an outer surface of the glass film 21 of the glass electrode 2. Further, in the region of the gate 10 which is sandwiched between the drain 13 and the source 14 of the reference electrode 1, the liquid 3 to be measured is in contact with the surface of the diamond thin film 12. On the other hand, due to the presence of the passivation layer 15, the liquid 3 to be measured is not in direct contact with the drain 13 and the source 14.

The internal electrode 23 is electrically connected to an inner wall of the glass film 21 via the internal liquid 22. As such, a potential depending on the inner wall of the glass film 21 is output to the output terminal 23A.

On the other hand, the potential of the gate 10 is controlled by a pseudo-reference electrode (not shown) in contact with the liquid 3 to be measured. When a potential is applied to the pseudo-reference electrode, the potential is given to the region sandwiched between the drain 13 and the source 14 via the liquid 3 to be measured. That is, it is possible to control the potential of the gate of the ISFET formed on the silicon wafer 11. The potential of the gate 10 of the ISFET and current of the gate 10 can be read out using an electric circuit such as a source follower circuit, for example, with a positive or negative potential (with respect to a drain voltage) supplied to the source 14.

Accordingly, the pH of the liquid to be measured can be calculated from the output potential of the output terminal 23A, i.e. the output potential of the glass electrode 2.

Further, aside from the aforementioned preferred embodiment, if the pseudo-reference electrode is not installed, the potential of the gate 10 of the reference electrode 1 may be controlled via the liquid 3 to be measured by applying a potential to the glass electrode 2, instead of controlling the potential of the gate 10 using the pseudo-reference electrode.

Next, a process of forming the diamond thin film 12 will be described.

Figure 3:
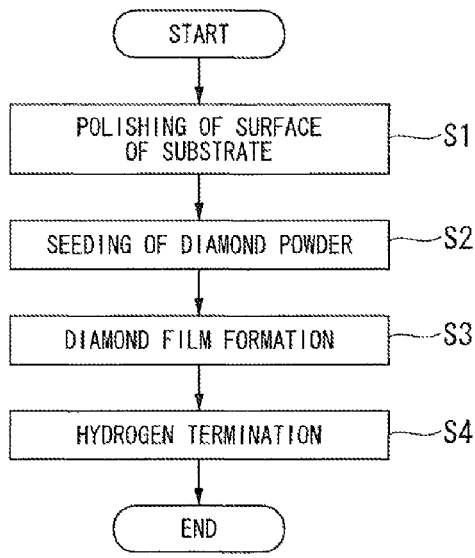
FIG. 3 is a flowchart illustrating a process of forming the diamond thin film of the pH sensor in accordance with the first preferred embodiment of the present invention.

FIG. 3 is a flowchart illustrating a process of forming the diamond thin film 12 of the pH sensor in accordance with the first preferred embodiment of the present invention.

In step S1 of FIG. 3, one surface of the silicon wafer 11 (substrate) is polished. To enhance adhesion of the silicon wafer 11 and the diamond layer, an arithmetic mean roughness Ra may be 0.1 to 15 μm, and a maximum height Rz may be set to 1 to 100 μm.

Next, seeding of diamond powder is performed in step S2.

In the process of step S2, to grow a uniform diamond layer, the seeding of diamond, is performed on one surface of the silicon wafer 11 that has been polished. As a seeding method, a method of applying a solution containing diamond particulates to the surface of the silicon wafer 11 using an ultrasonic method, a dipping method, or another method, and solvent-drying the applied surface may be used.

Next, a process of forming a film of diamond is performed in step S3.

In the process of step S3, a film of diamond is formed by a hot filament CVD method. A carbon source (e.g., a low molecular weight organic compound such as methane, alcohol, or acetone) is supplied to a filament along with hydrogen gas. The silicon wafer 11 is disposed so as to heat the filament to a temperature region (e.g., 1800 to 2800° C.) at which carbon radicals are generated, and to reach a temperature region (e.g., 750 to 950° C.) at which the diamond is precipitated in this heated atmosphere. Although the supply rate of a mixed gas is dependent on the size of a reaction container, pressure may range from 15 to 760 Torr. A layer of the diamond particulates whose diameter typically ranges from 0.001 to 2 μm is precipitated on the silicon wafer. The thickness of the diamond particulate layer may be adjusted by deposition time, but it may be 0.5 to 20 μM from an economical viewpoint.

Next, hydrogen termination of as-grown diamond is performed in step S4.

In the process of step S4, a hydrogen terminal is substituted for a terminal (e.g., a carbon terminal or an oxygen terminal) other than the hydrogen terminal of as-grown diamond after the formation of the diamond film, thereby increasing the density. As the method of performing the high-density hydrogen termination, any one of hydrofluoric acid solution based treatment, hydrogen plasma treatment, heating in a hydrogen atmosphere, hydrogen radical treatment, and a cathodic reduction method may be selected. The efficiency of the hydrogen termination may be enhanced by a combination of two or more methods.

As the hydrogen plasma treatment, for example, hydrogen density of the diamond terminal may become high on treatment conditions of 1 kW, a $H_2$-flow rate of 400 sccm, and plasma irradiation time of 5 hours. Further, as the cathodic reduction method, for example, a method of applying voltage of about −1.8 V to a conductive diamond electrode in an as-grown state, and dipping the electrode into a sulfuric acid solution ($H_2SO_4$) of 0.1 M for 30 minutes or more may be used.

Further, the process of step S1, step S2, or step S4 may be omitted.

Quality and quantity of the hydrogen terminal on the diamond surface formed by the aforementioned processes may be examined by an analysis method known from the related art such as X-ray photoelectron spectroscopy (XPS), a secondary ion mass spectrometer (SIMS), or a Fourier transform infrared (FT-IR) spectrophotometer. Thereby, the diamond thin film 12 is formed.

Next, an example of a process of fabricating a diamond ISFET on the silicon wafer 11 on which the diamond thin film 12 is formed will be described.

First, the surface of the diamond thin film 12 is partially subjected to oxygen termination. In this process, the surface of the diamond thin film 12 is spin-coated with a resist, and the coated resist is patterned by exposure and development.

Then, only the exposed region of the diamond thin film 12 is selectively oxygen-terminated by oxygen reactive ion etching (RIE), and the resist is removed by a solvent and ultrasonic irradiation. In this process, the region of the gate 10 which is sandwiched between the drain 13 and the source 14 and is in contact with the diamond thin film 12 and the liquid to be measured, and the lower regions of the drain 13 and the source 14 are not subjected to the oxygen termination.

Next, the surface of the diamond thin film 12 is spin-coated with a resist, and the coated resist is patterned by exposure and development. Then, a Au/Ti thin film having a pattern shown in FIG. 2 is formed on the diamond thin film 12 by Au/Ti sputtering and lift-off. Thereby, the drain 13 and the source 14 are formed.

Subsequently, the substrate on which the diamond thin film 12 and the Au/Ti thin film are formed is spin-coated with a resist that becomes a passivation layer 15, and the coated resist is patterned by exposure and development. In a region from which the resist is removed, the diamond thin film 12 is in an exposed state. The gate 10 between the drain 13 and the source 14 corresponds to the resist-free region. In the resist-free region, the liquid to be measured is in direct contact with the diamond thin film 12.

In the aforementioned preferred embodiment, the silicon wafer is used as the substrate by way of example. However, a material for the substrate may be arbitrary.

Further, a method of supporting the diamond thin film on the substrate is not limited to the aforementioned method, and so an arbitrary method may be used. As the representative film formation method, a vapor phase synthetic method may be used. The vapor phase synthetic method includes a chemical vapor deposition (CVD) method, a physical vapor deposition (PVD) method, or a plasma jet method. Further, the CVD method includes a hot filament CVD method or a microwave plasma CVD method.

Further, regardless of which diamond film formation method is used, the synthesized diamond layer may have a polycrystalline structure, and an amorphous carbon or graphite component may remain in the diamond layer. Regarding the stability of the diamond layer, it is advantageous for the amorphous carbon or graphite component to remain as small as possible, for a ratio I (D)/I (G) of peak intensity I (D) existing around 1332 cm$^{-1}$ (a range of 1321 to 1352 cm$^{-1}$) belonging to the diamond to a peak intensity I (G) around 1580 cm$^{-1}$ (a range of 1560 to 1600 cm$^{-1}$) belonging to a G band of the graphite to be 1 or more in the Raman spectroscopic analysis, and for the content of the diamond to be more than that of the graphite.

Instead of forming the diamond thin film on the substrate, an independent diamond bulk may be used without using a substrate formed of silicon or carbon.

The hydrogen-terminated diamond thin film 12 is disposed on the portion of the gate 10 of the diamond ISFET. However, the portion of the gate 10 may become the diamond surface having a hydrogen ion insensitive terminal, and thus is not limited to the case in which the hydrogen termination is performed.

In the present invention, the conditions required for the diamond surface of the gate portion of the diamond ISFET are as follows: When a concentration of hydrogen ions ranges from $1.0 \times 10^{-1}$ mol/L to $1.0 \times 10^{-14}$ mol/L, a terminal element is controlled so as to cause the potential to be stabilized, or to cause the uniformity of the potential to be maintained to such an extent that the ion sensitivity has no practical issue. Thereby, the reference electrode becomes a solid structure in which no internal liquid is contained, and thus it is possible to avoid the problem caused by the internal liquid like the glass electrode in the related art.

As such a diamond surface in which the potential is stabilized or the ion sensitivity has no practical issue when the concentration of hydrogen ions ranges from $1.0 \times 10^{-1}$ mol/L to $1.0 \times 10^{-14}$ mol/L, diamond in which the hydrogen density of as-grown diamond is increased by hydrogen plasma treatment, diamond in which hydrogen terminal diamond is partially oxygen-terminated, diamond in which hydrogen terminal diamond is partially oxygen-terminated, or diamond in which hydrogen terminal diamond is partially fluorine-terminated may be used.

Figure 4:
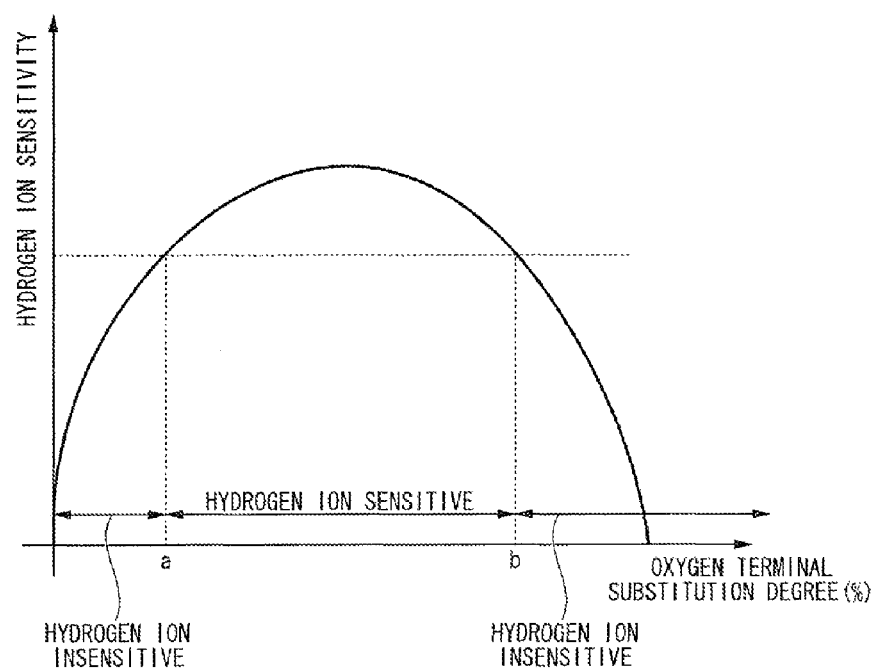
FIG. 4 is a characteristic diagram illustrating a relation between hydrogen ion sensitivity and a degree of substitution of an oxygen terminal.

FIG. 4 is a characteristic diagram illustrating a relation between hydrogen ion sensitivity and a degree of substitution of an oxygen terminal, in which a longitudinal axis shows the hydrogen ion sensitivity and a transverse axis shows the oxygen terminal substitution degree. The oxygen terminal substitution degree used herein can be expressed by the following formula:

Oxygen Terminal Substitution Degree=$A/(A+B)$ where A refers to the number of carbon atoms on the diamond surface of the oxygen terminal, and B refers to the number of carbon atoms on the diamond surface other than the oxygen terminal.

The oxygen terminal substitution degree of 0% refers to a diamond surface where no oxygen terminal is present. The oxygen terminal substitution degree of 100% refers to a diamond surface where only the oxygen terminal is present. For example, the oxygen terminal substitution degree of the as-grown diamond that has been hydrogen-terminated has a value of approximately 0%.

As shown in FIG. 4, as the oxygen terminal substitution degree increases from 0%, the hydrogen ion sensitivity increases, and is eventually changed into reduction. When the oxygen terminal substitution degree exceeds a constant value, the hydrogen ion sensitivity is approximately zero. In the gate portion of the present invention, for example, the oxygen terminal substitution degree having a range within which the ion insensitivity of FIG. 4 can be obtained, i.e. a range equal to or less than a % or a range equal to or greater than b %, is selected.

Further, a hydrogen ion insensitive terminal in which an oxygen terminal or a fluorine terminal is substituted for part of hydrogen terminals of the as-grown diamond that has been hydrogen-terminated may be used in the gate portion.

As described above, according to the present invention, in the ISFET of the terminal control diamond, the liquid electrolyte is adopted as the liquid to be measured and the gate is used as the reference electrode, so that it is possible to realize the pH sensor having a reference electrode that is excellent in high-temperature and high-pressure, is acid and alkali resistant, and requires no internal liquid.

Thereby, it is possible to overcome the problem with leakage or time degradation of the internal liquid, which is the problem of the reference electrode of a type where the internal liquid is contained. Further, it is possible to provide a pH sensor that enables accurate measurement in the bioprocess of processing bio-related materials such as proteins, for example, under strong-acid or -alkaline conditions of the semiconductor fabricating process of the chemical synthesis plant, and that contributes to visualization of a pH value in a production process.

As a type of the diamond used in the diamond ISFET of the present invention, a signal crystal diamond may be used in addition to the exemplified polycrystalline diamond. Further, along with conductive diamond (doped diamond: polycrystal or single crystal), an elemental substance such as diamond-like carbon, conductive diamond-like carbon (doped diamond-like carbon), electron cyclotron resonance (ECR) sputtered carbon, radio frequency (RF) sputtered carbon, carbon nanotube, fullerene, or carbon nanotube, and a conductive carbon material consisting essentially of one thereof may be used. Like the diamond, the ECR sputtered carbon, and the diamond-like carbon, a structure in which a ratio of $sp^3$ to $sp^2$ (an $sp^3/sp^2$ ratio) is mainly high is more preferable. Diamond having the highest $sp^3$ fraction is the most preferable in practicing the present invention.

When the conductive diamond thin film (doped diamond) is supported, mixed gas of hydrogen and a carbon source is used as a diamond raw material in any method. To impart conductivity to the diamond, a trace of an element (dopant) whose valence is different from that of the diamond may be added. The dopant may include boron, phosphorus, or nitrogen, and may have a content of 1 to 100,000 ppm, preferably 100 to 10,000 ppm.

In the preferred embodiment above, the glass electrode has been used as the working electrode by way of example, but the type of working electrode is not limited.

Figure 5:
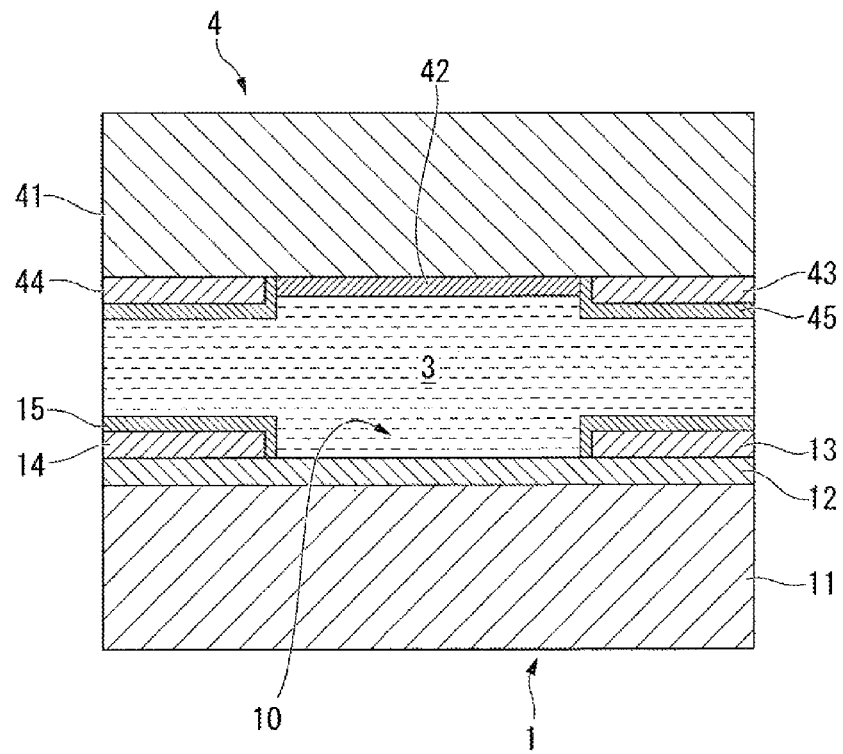
FIG. 5 is a cross-sectional view illustrating the construction of a pH sensor in accordance with a second preferred embodiment of the present invention.

FIG. 5 is a cross-sectional view illustrating the construction of a pH sensor in accordance with a second preferred embodiment of the present invention. In detail, FIG. 5 is a cross-sectional view illustrating the construction of a pH sensor in which a p-type silicon semiconductor (ISFET) is used as a working electrode. In FIG. 5, the same elements as in FIG. 1 are given the same numerals.

As shown in FIG. 5, the working electrode 4 adopting the p-type silicon semiconductor (ISFET) includes a drain 43 formed on a substrate 41, a source 44 formed on the substrate 41 at a position opposite the drain 43, a passivation layer 45 covering the drain 43 and the source 44, and a thin gate insulating layer 42 formed on the portion of a gate between the drain 43 and the source 44 on the substrate 41. The gate insulating layer 42 has ion sensitivity. As the gate insulating layer 42, for example, tantalum pentoxide ($Ta_2O_5$) may be used.

When pH is measured, the liquid 3 to be measured is in contact with the gate insulating layer 42 of the working electrode 4 and the gate portion of the diamond thin film 12 of the reference electrode 1.

A potential is applied to the liquid 3 to be measured via a pseudo-reference electrode (not shown) that is electrically in contact with the pseudo-reference electrode (not shown).

The potential of the gate 10 of the working electrode 4 and current of the gate 10 may be read out using an electric circuit such as a source follower circuit, for example, with a positive or negative potential (with respect to a drain voltage) supplied to the source 44. Further, the potential of the gate 10 may be read out using an electric circuit such as a source follower circuit, for example, with a positive or negative potential (with respect to a drain voltage) supplied to the source 14.

The pH of the liquid 3 to be measured is calculated based on a difference between a potential of the working electrode 4 and a potential of the reference electrode 1.

Next, an example of compensating for a temperature of the diamond ISFET will be described with reference to FIGS. 6 and 7.

Figure 6:
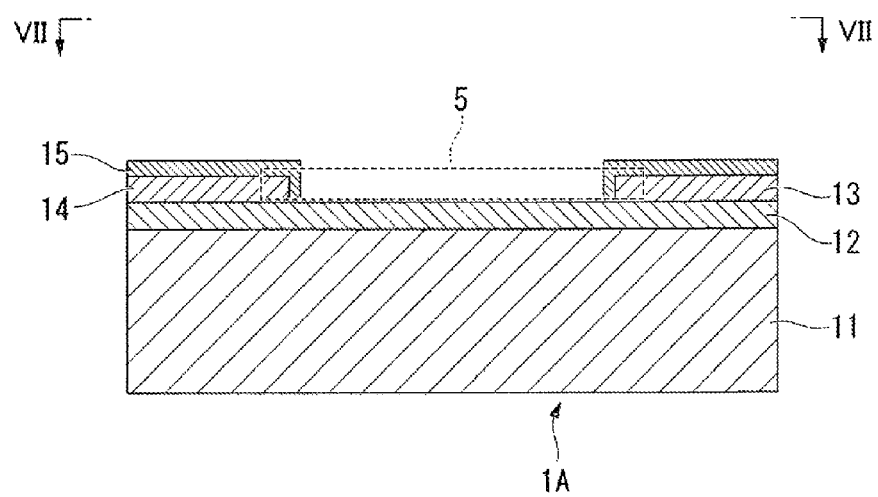
FIG. 6 is a cross-sectional view illustrating the construction of a reference electrode for a pH sensor in accordance with a third preferred embodiment of the present invention.

FIG. 6 is a cross-sectional view illustrating the construction of a reference electrode for a pH sensor in accordance with a third preferred embodiment of the present invention. FIG. 6 is a cross-sectional view illustrating the construction of a reference electrode on which a thermistor is installed. FIG. 7 is a plan view of the ISFET portion of FIG. 6, when viewed from a line VII-VII of FIG. 6. In FIGS. 6 and 7; the same elements as in FIGS. 1 and 2 are given the same numerals.

Figure 7:
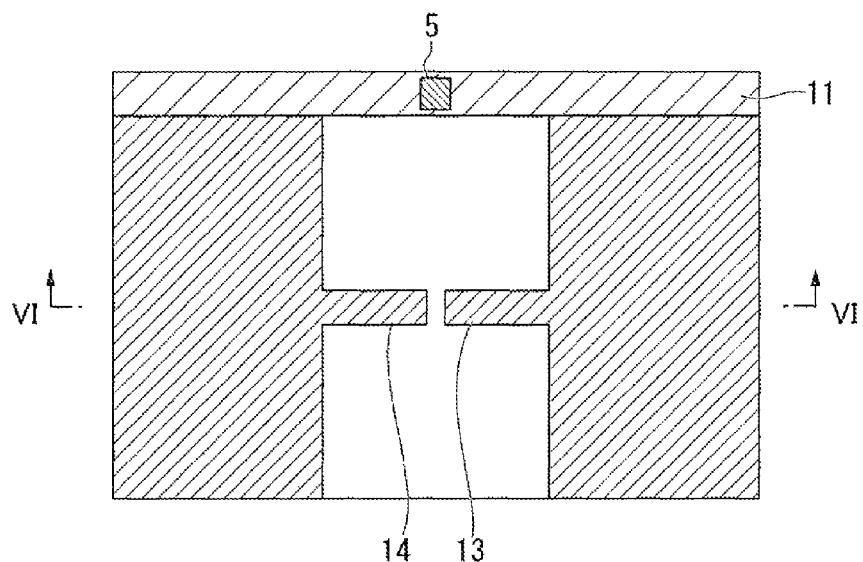
FIG. 7 is a plan view of the ISFET portion of the reference electrode for the pH sensor in accordance with the third preferred embodiment of the present invention.

As shown in FIGS. 6 and 7, a thermistor 5 is formed as a temperature sensor on the silicon wafer 11 of a reference electrode 1A. A temperature characteristic of the ISFET is compensated for based on a change in resistance value of the thermistor 5. In this case, it is possible to accurately measure pH at all times regardless of the temperature of the liquid to be measured. Similarly, such temperature compensation can also be performed on an output value of the working electrode based on the change of the resistance value of the thermistor 5.

The reference electrode shown in FIGS. 6 to 7 may be used by a combination with an arbitrary working electrode, aside from the glass electrode or the ISFET using the p-type silicon semiconductor.

As described above, in the pH sensor in accordance with the preferred embodiment of the present invention, since the reference electrode is formed as the p-channel PET, the problem with leakage or time degradation of the internal liquid in the reference electrode can be resolved.

The application of the present invention is not limited to the preferred embodiments above. The present invention may be widely applied to pH sensors, each of which includes a reference electrode and a working electrode, and measures pH of a liquid to be measured based on outputs of the reference electrode and the working electrode.

Hereinafter, an preferred embodiment in which an ion sensor in accordance with the present invention is applied to the pH sensor will be described.

Figure 8:
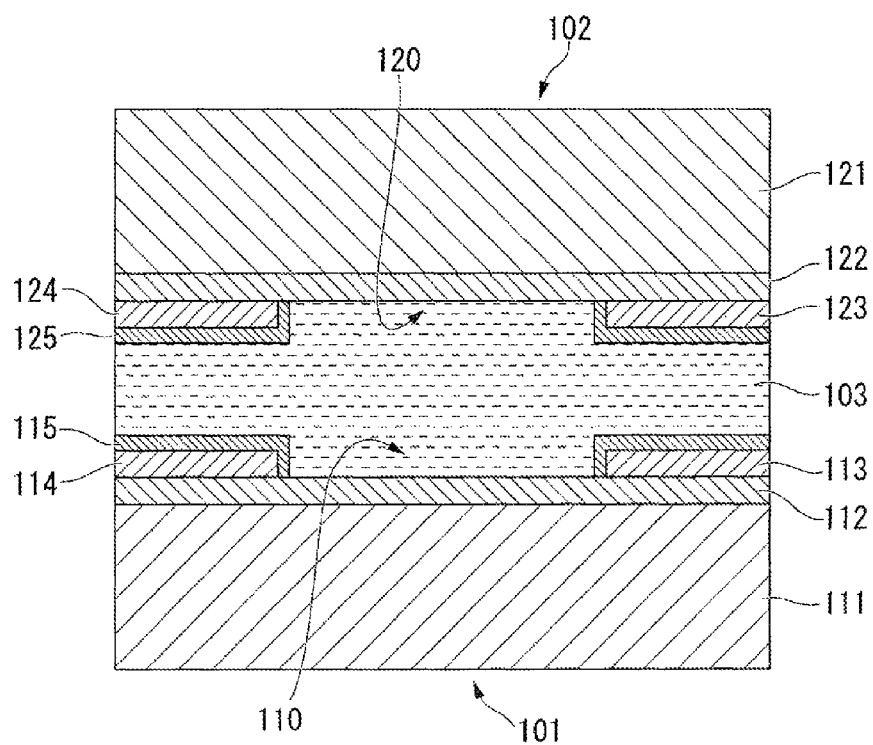
FIG. 8 is a cross-sectional view illustrating the construction of a pH sensor in accordance with a fourth preferred embodiment of the present invention.
Figure 9:
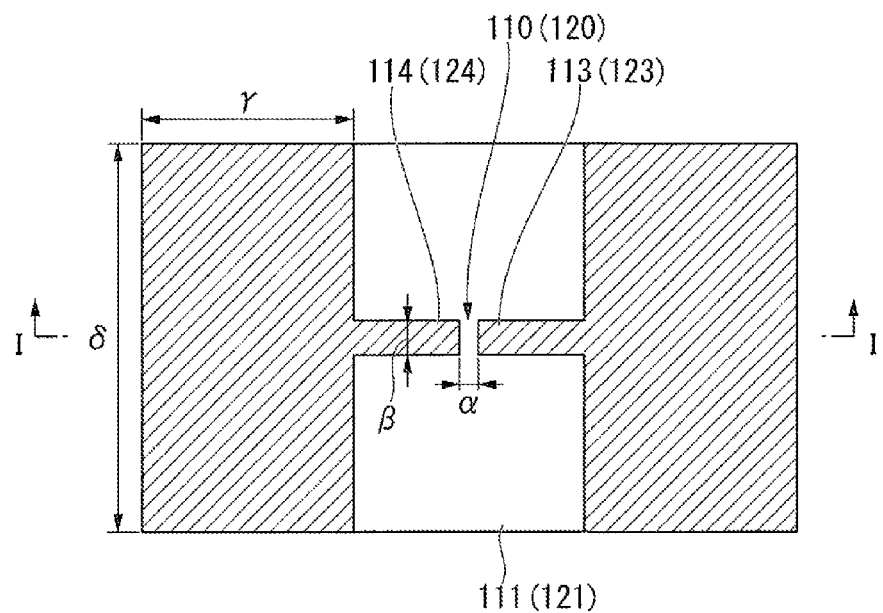
FIG. 9 is a plan view illustrating shapes of a drain and a source of the reference electrode and the working electrode of the pH sensor in accordance with the fourth preferred embodiment of the present invention.

FIG. 8 is a cross-sectional view illustrating the construction of a pH sensor in accordance with a fourth preferred embodiment of the present invention. FIG. 9 is a plan view illustrating shapes of a drain 113 (123) and a source 114 (124) of the reference electrode 101 and the working electrode 102 of FIG. 8.

As shown in FIGS. 8 and 9, as an ion sensor in accordance with a fourth preferred embodiment of the present invention, a pH sensor uses diamond ISFETs as the reference electrode 101 and the working electrode 102, respectively.

As shown in FIGS. 8 and 9, the reference electrode 101 includes a silicon wafer 111 on which a diamond thin film 112 is formed, a drain 113 formed on a surface of the diamond thin film 112, a source 114 formed on the surface of the diamond thin film 112 so as to be opposite to the drain 113, and a passivation layer 115 covering the drain 113 and the source 114. In this pH sensor, a region sandwiched between the drain 113 and the source 114 functions as a gate 110. The drain 113, the source 114, and the gate 110 form a p-channel FET. This p-channel FET is an ion sensitive field effect transistor (ISFET). Further, the p-channel FET is also called a diamond ISFET because it has a diamond thin film.

An arbitrary numerical value may be applied to the size, intervals and the like, of the electrodes of the drain 113 and the source 114. For example, in FIG. 9, a distance a between the drain 113 and the source 114 may be 10 to 1000 µm, a width β of the ISFET portion of the source 114 (or a width of the ISFET portion of the drain 113) may be 0.01 to 50 mm, a length γ of the source 114 (or a length of the drain 113) may be 5 to 50 mm, and a width δ of the source 114 (or a width of the drain 113) may be 5 to 100 mm.

In a portion of the gate 110 of the reference electrode 101, the surface of the diamond thin film 112 is configured so that, when a concentration of hydrogen ions ranges from $1.0 \times 10^{-1}$ mol/L to $1.0 \times 10^{-14}$ mol/L, a terminal element is controlled so as to cause the potential to be stabilized, or to cause the uniformity of the potential to be maintained to such an extent that the ion sensitivity has no practical issue.

As such a diamond surface in which the potential is stabilized or the ion sensitivity has no practical issue when the concentration of hydrogen ions ranges from $1.0 \times 10^{-1}$ mol/L to $1.0 \times 10^{-14}$ mol/L, diamond in which the hydrogen density is increased by hydrogen plasma treatment, diamond in which hydrogen terminal diamond is partially oxygen-terminated, diamond in which hydrogen terminal diamond is partially oxygen-terminated, or diamond in which hydrogen terminal diamond is partially fluorine-terminated may be used.

As shown in FIG. 8, the working electrode 102 is installed so as to be opposite to the reference electrode 101. As shown in FIGS. 8 and 9, the working electrode 102 includes a silicon wafer 121 on which the diamond thin film 122 is formed, a drain 123 formed on a surface of the diamond thin film 112, a source 124 formed on the surface of the diamond thin film 122 so as to be opposite to the drain 123, and a passivation layer 125 covering the drain 123 and the source 124. In this pH sensor, a region sandwiched between the drain 123 and the source 124 functions as a gate 120.

The drain 123 and the source 124 may have the same shape as the drain 113 and the source 114 of the reference electrode 101 shown in FIG. 9, respectively. The sizes, intervals and the like, of the electrodes of the drain 123 and the source 124 may be different from those of the reference electrode 101. However, even in this case, in FIG. 9, a may range from 10 to 1000 μm, β may range from 0.01 to 50 mm, γ may range from 5 to 50 mm, and δ may range from 5 to 100 mm.

In a portion of the gate 120 of the reference electrode 102, the surface of the diamond thin film 112 is configured so that, when a concentration of hydrogen ions ranges from $1.0 \times 10^{-1}$ mol/L to $1.0 \times 10^{-14}$ mol/L, a terminal element is controlled so as to cause the potential to make a linear or non-linear response depending on pH value.

As such a diamond surface in which the potential makes a linear or non-linear response depending on pH value when the concentration of hydrogen ions ranges from $1.0 \times 10^{-1}$ mol/L to $1.0 \times 10^{-14}$ mol/L, diamond in which diamond whose hydrogen density is increased by hydrogen plasma treatment is partially oxygen-terminated so as to be a hydrogen ion sensitive terminal or is substituted by an amino terminal may be used.

In the second p-channel FET of the working electrode 102, sensitivity (Nernst response) to measuring-target ions of a terminal of a semiconductor surface of the gate 120 portion is a voltage of the working electrode 102 depending on an ion concentration.

In the first p-channel FET of the reference electrode 101, sensitivity (Nernst response) to measuring-target ions of a terminal of a semiconductor surface of the gate 110 portion is a voltage of the working electrode 102 depending on an ion concentration.

The sensitivity to the measuring-target ions of the terminal of the semiconductor surface of the gate 120 portion becomes higher than the sensitivity to the measuring-target ions of the terminal of the semiconductor surface of the gate 110 portion.

Next, an operation of the pH sensor will be described.

As shown in FIG. 8, in the region of the gate 110 which is sandwiched between the drain 113 and the source 114 of the reference electrode 101, the liquid 103 to be measured is in contact with the surface of the diamond thin film 112. On the other hand, due to the presence of the passivation layer 115, the liquid 103 to be measured is not in direct contact with the drain 113 and the source 114.

Further, in the region of the gate 120 which is sandwiched between the drain 123 and the source 124 of the reference electrode 102, the liquid 103 to be measured is in contact with the surface of the diamond thin film 122. On the other hand, due to the presence of the passivation layer 125, the liquid 103 to be measured is not in direct contact with the drain 123 and the source 124.

A potential of the liquid 103 to be measured is controlled by a pseudo-reference electrode (not shown) that is in contact with the liquid 103 to be measured. When a potential is applied to the pseudo-reference electrode, the potential is given to the region of the gate 110 sandwiched between the drain 113 and the source 114 of the reference electrode 101 via the liquid 103 to be measured, and simultaneously to the region of the gate 120 sandwiched between the drain 123 and the source 124 of the reference electrode 101 via the liquid 103 to be measured. In this way, the potential of the gate 110 of the reference electrode 101, and the potential of the gate 120 of the working electrode 102 are controlled.

Figure 10:
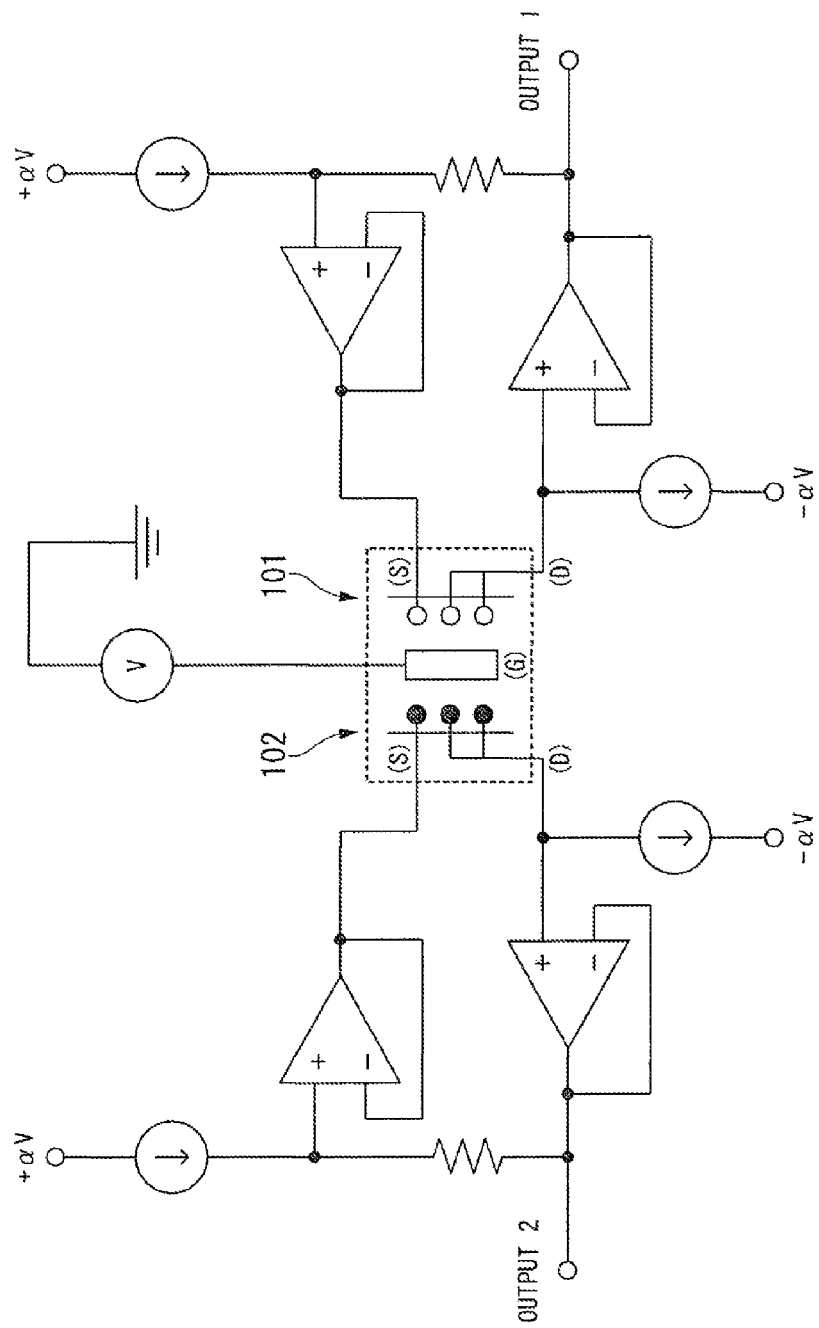
FIG. 10 is a view illustrating an example of a circuit that measures pH of the liquid 3 to be measured using the pH sensor in accordance with the fourth preferred embodiment of the present invention.

FIG. 10 shows an example of a circuit that measures pH of the liquid 103 to be measured using the pH sensor of FIG. 8. A predetermined voltage V is applied to the pseudo-reference electrode G. The pseudo-reference electrode G is in contact with the liquid 103 to be measured (not shown). A constant current source and a buffer are connected to a drain D of the reference electrode 101. A buffer is connected to a source S of the reference electrode 101. Output 1 is connected to the drain D of the reference electrode 101 via the buffer, and is connected to the source S of the reference electrode 101 via a resistor and the buffer. A constant current source and a buffer are connected to a drain D of the working electrode 102. A buffer is connected to a source S of the working electrode 102. Output 2 is connected to the drain D of the working electrode 102 via the buffer, and is connected to the source S of the working electrode 102 via a resistor and the buffer.

In the example of the circuit of FIG. 10, when the voltage V (with respect to an earth potential) is applied to the liquid 103 to be measured via the pseudo-reference electrode G, potentials are generated from a gate 110 of the reference electrode 101 and a gate 120 of the working electrode 102, respectively.

In the circuit of FIG. 10, voltage occurs at the output 1 based on the drain D and the source S of the reference electrode 101, and voltage occurs at the output 2 based on the drain D and the source S of the working electrode 102. Thus, a difference between the voltage value of the output 1 and the voltage value of the output 2 has a correlation with the pH of the liquid 103 to be measured.

Figure 11:
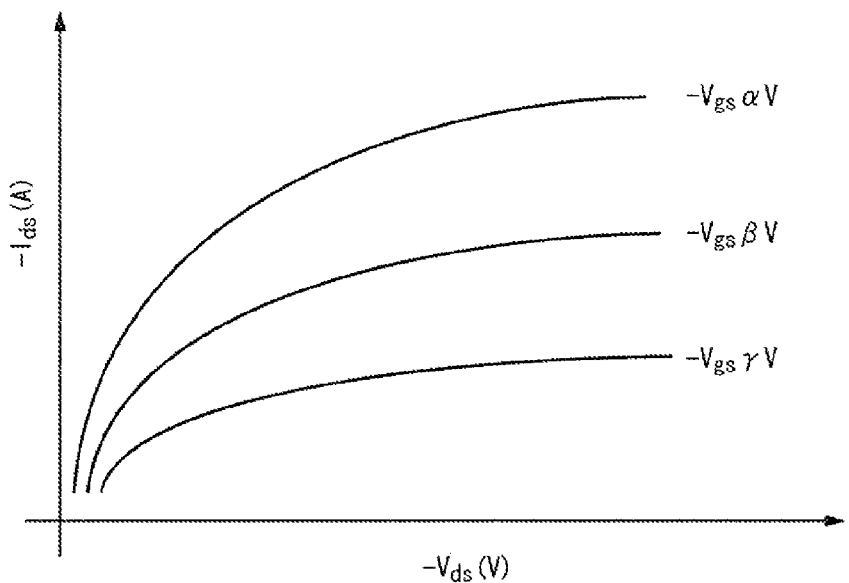
FIG. 11 is a view illustrating drain-source characteristics of the pH sensor in accordance with the fourth preferred embodiment of the present invention.

FIG. 11 shows drain-source characteristics of the pH sensor of FIG. 8. The transverse axis indicates voltage "−Vds (V)" between the drain 113 (123) and the source 114 (124), and the longitudinal axis indicates current "−Ids (A)" between the drain 113 (123) and the source 114 (124). A current "−Ids (A)" to voltage "−Vds (V)" characteristic when voltage −Vgs of the pseudo-reference electrode G is constant at −α (V), a current "−Ids (A)" to voltage "−Vds (V)" characteristic when voltage −Vgs of the pseudo-reference electrode G is constant at −β (V), and a current "−Ids (A)" to voltage "−Vds (V)" characteristic when voltage −Vgs of the pseudo-reference electrode G is constant at −γ (V) are shown. When α(V)>β(V)>γ(V), a characteristic curve when the voltage −Vgs=−α(V)>a characteristic curve when the voltage −Vgs=−β(V)>a characteristic curve when the voltage −Vgs=−γ(V).

The pH sensor is characterized in that the characteristic curve of FIG. 11 moves upwards when the pH value of the liquid 103 to be measured increases, and that the characteristic curve of FIG. 11 moves downwards when the pH value of the liquid 103 to be measured decreases.

Figure 12:
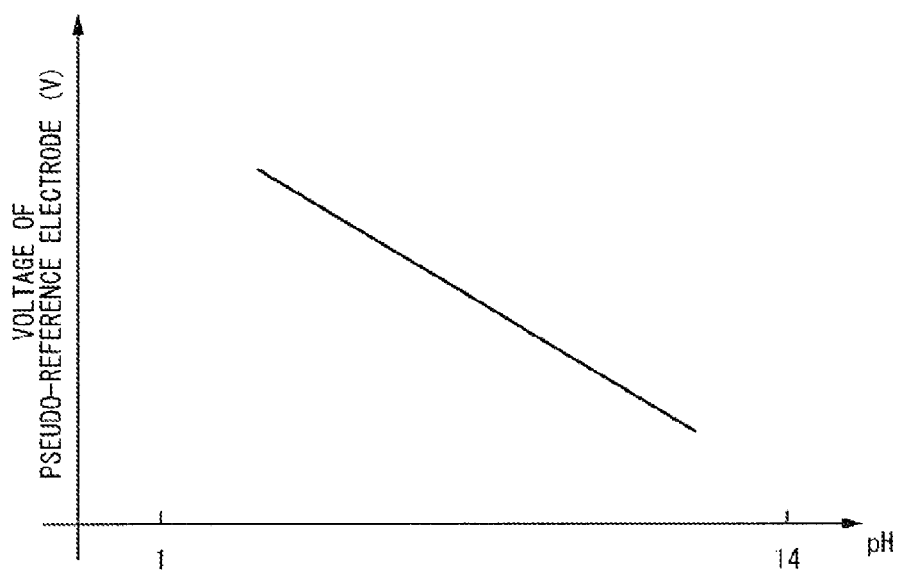
FIG. 12 is a view illustrating a pH-voltage characteristic of the pH sensor in accordance with the fourth preferred embodiment of the present invention.

FIG. 12 shows a pH-voltage characteristic of the example of the circuit of FIG. 10. The transverse axis indicates a pH value of the liquid 103 to be measured, and the longitudinal axis indicates voltage Vgs of the pseudo-reference electrode G.

When the current "−Ids (A)" between the drain 113 (123) and the source 114 (124) is constant, if the pH value of the liquid 103 to be measured is increased, it shows a characteristic that the voltage Vgs of the pseudo-reference electrode G is lowered. With use of this characteristic, the pH value of the liquid 103 to be measured is calculated from the voltage Vgs of the pseudo-reference electrode G.

When the pH value of the liquid 103 to be measured is increased on specific conditions, it shows a characteristic in which the voltage Vgs of the pseudo-reference electrode G may be raised. Further, when the pH value of the liquid 103 to be measured is increased on specific conditions, it shows a characteristic in which the voltage Vgs of the pseudo-reference electrode G may vary in a non-linear pattern. In this case, the value of the voltage Vgs of the pseudo-reference electrode G and the pH value of the liquid 103 to be measured are correlated, and thus the pH value of the liquid 103 to be measured can be calculated from the value of the voltage Vgs of the pseudo-reference electrode G.

Next, a film formation process for each of the diamond thin film 112 and the diamond thin film 122 will be described.

Figure 13:
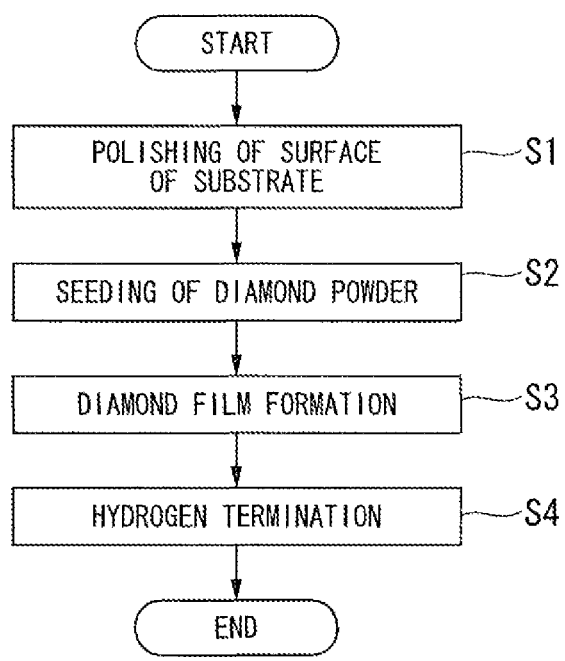
FIG. 13 is a flowchart illustrating a film formation process for a diamond thin film of the pH sensor in accordance with the fourth preferred embodiment of the present invention.

FIG. 13 is a flowchart illustrating a film formation process for a diamond thin film of the pH sensor in accordance with the fourth preferred embodiment of the present invention.

In step S1 of FIG. 13, the surface of a silicon wafer 111 or 121 is polished. To enhance adhesion of the silicon wafer 111 or 121 and a diamond layer, an arithmetic mean roughness Ra may be set to 0.1 to 15 μm, and a maximum height Rz may be set to 1 to 100 μm.

Next, seeding of diamond powder is performed in step S2.

In the process of step S2, to grow a uniform diamond layer, the seeding of diamond is performed on a surface of the silicon wafer 111 or 121 that has been polished. As a seeding method, a method of applying a solution containing diamond particulates to the surface of the silicon wafer 111 or 121 using an ultrasonic method, a dipping method, or another method, and solvent-drying the applied surface may be used.

Next, a process of forming a film of diamond is performed in step S3.

In the process of step S3, a film of diamond is formed by a hot filament CVD method. A carbon source (e.g., a low molecular weight organic compound such as methane, alcohol, or acetone) is supplied to a filament along with hydrogen gas. The silicon wafer 111 is disposed so as to heat the filament to a temperature region (e.g., 1800 to 2800° C.) at which carbon radicals are generated, and to reach a temperature region (e.g., 750 to 950° C.) at which the diamond is precipitated in this heated atmosphere. Although the supply rate of a mixed gas is dependent on the size of a reaction container, pressure may range from 15 to 760 Torr. A layer of the diamond particulates whose diameter typically ranges from 0.001 to 2 μm is precipitated on the silicon wafer. The thickness of the diamond particulate layer may be adjusted by deposition time, but it may be 0.5 to 20 μm from an economical viewpoint.

Next, hydrogen termination is performed on as-grown diamond in step S4.

In the process of step S4, a hydrogen terminal is substituted for a terminal (e.g., a carbon terminal or an oxygen terminal) other than the hydrogen terminal of as-grown diamond after the diamond film formation, thereby increasing the density. As the method of performing the high-density hydrogen termination, any one of hydrofluoric acid solution based treatment, hydrogen plasma treatment, heating in a hydrogen atmosphere, hydrogen radical treatment, and a cathodic reduction method may be selected. The efficiency of the hydrogen termination may be enhanced by a combination of two or more methods.

As the hydrogen plasma treatment, for example, hydrogen density of the diamond terminal may become high under the treatment condition of 1 kW, a $H_2$-flow rate of 400 sccm, and plasma irradiation time of 5 hours. Further, as the cathodic reduction method, for example, a method of applying voltage of about −1.8 V to a conductive diamond electrode in an as-grown state, and dipping the electrode into a sulfuric acid solution ($H_2SO_4$) of 0.1 M for 30 minutes or more may be used.

Further, the process of step S1, step S2, or step S4 may be omitted.

Quality and quantity of the hydrogen terminal on the diamond surface formed by the aforementioned processes may be examined by an analysis method known from the related art such as X-ray photoelectron spectroscopy (XPS), a secondary ion mass spectrometer (SIMS), or a Fourier transform infrared (FT-IR) spectrophotometer.

Next, an example of a process of fabricating a diamond ISFET on the silicon wafer 111 or 12I on which the diamond thin film 112 or 122 is formed will be described.

First, the surface of the diamond thin film 112 or 122 is partially subjected to oxygen termination. In this process, the surface of the diamond thin film 112 or 122 is spin-coated with a resist, and the coated resist is patterned by exposure and development. Then, only the exposed region of the diamond thin film 112 or 122 is selectively oxygen-terminated by oxygen reactive ion etching (RIE), and the resist is removed by a solvent and ultrasonic irradiation. In this process, the region of the gate 110 which is sandwiched between the drain 113 and the source 114, and is in contact with the diamond thin film 112 of the reference electrode 101 and the liquid to be measured, and the lower regions of the drain 113 and the source 114 are not subjected to the oxygen termination. A region other than the region of the gate 110, a region other than the lower region of the drain 113, and a region other than the lower region of the source 114 are subjected to the oxygen termination.

Next, the surface of the diamond thin film 112 or 122 is spin-coated with a resist, and the coated resist is patterned by exposure and development. Then, a Au/Ti thin film having a pattern shown in FIG. 9 is formed on the diamond thin film 112 or 122 by Au/Ti sputtering and lift-off. Thereby, the drain 113 or 123 and the source 114 or 124 are formed.

Subsequently, the substrate on which the diamond thin film 112 or 122 and the Au/Ti thin film are formed is spin-coated with a resist that becomes a passivation layer 115 or 125, and the coated resist is patterned by exposure and development. In a region from which the resist is removed, the diamond thin film 112 or 122 is in an exposed state. The gate 110 or 120 between the drain 113 or 123 and the source 114 or 124 corresponds to the resist-free region. In the resist-free region, the liquid 10 to be measured is in direct contact with the diamond thin film 112 or 122.

In the aforementioned preferred embodiment, the silicon wafer is used as the substrate by way of example. However, a material for the substrate may be arbitrary.

Further, a method of supporting the diamond thin film on the substrate is not limited to the aforementioned method, and so an arbitrary method may be used. As the representative film formation method, a vapor phase synthetic method may be used. The vapor phase synthetic method includes a chemical vapor deposition (CVD) method, a physical vapor deposition (PVD) method, or a plasma jet method. Further, the CVD method includes a hot filament CVD method or a microwave plasma CVD method.

Further, regardless of which diamond film formation method is used, the synthesized diamond layer may have a polycrystalline structure, and an amorphous carbon or graphite component may remain in the diamond layer. Regarding the stability of the diamond layer, it is advantageous for the amorphous carbon or graphite component to remain as small as possible, for a ratio I (D)/I (G) of peak intensity I (D) existing around 1332 cm$^{-1}$ (a range of 1321 to 1352 cm$^{-1}$) belonging to the diamond to a peak intensity I (G) around 1580 cm$^{-1}$ (a range of 1560 to 1600 cm$^{-1}$) belonging to a G band of the graphite to be 1 or more in the Raman spectroscopic analysis, and for the content of the diamond to be more than that of the graphite.

Instead of forming the diamond thin film on the substrate, an independent diamond bulk may be used without using a substrate formed of silicon or carbon.

Figure 14A:
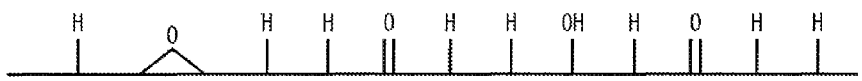
FIGS. 14A, 14B, 14C and 14D are diagrams illustrating terminal states of thin film surface of diamond.
Figure 14B:
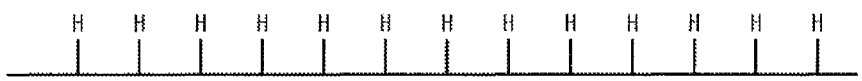
Figure 14C:
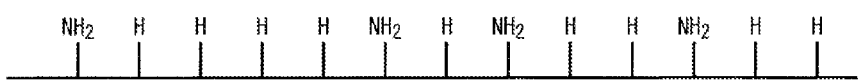
Figure 14D:
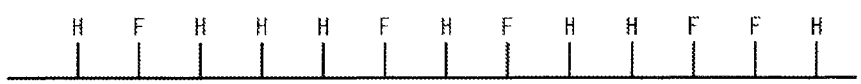

FIGS. 14A to 14D are schematic views illustrating a terminal state of the surface of the diamond thin film 112. FIG. 14A shows a terminal state of as-grown diamond. FIG. 14B shows a terminal state of diamond that is hydrogen-terminated. FIG. 14C shows a terminal state of diamond that is partially amino-terminated. FIG. 14D shows a terminal state of diamond that is partially fluorine-terminated.

The hydrogen-terminated diamond thin film 112 is disposed on the portion of the gate 110 of the reference electrode 101. However, the portion of the gate of the reference electrode may become the diamond surface having a hydrogen ion insensitive terminal, and thus is not limited to the case in which the hydrogen termination is performed. For example, there is hydrogen-terminated diamond (FIG. 14B), diamond in which an element having hydrogen ion insensitivity is substituted for part of hydrogen terminals of the hydrogen-terminated diamond, partial fluorine terminal diamond (FIG. 14D), or partial oxygen terminal diamond.

Further, as the hydrogen terminal diamond of the portion of the gate of the working electrode, diamond in which an element having a hydrogen ion sensitive effect is substituted for part of hydrogen terminals of the hydrogen-terminated diamond, for example partial amino terminal diamond (FIG. 14C) or partial oxygen terminal diamond, may be used.

Figure 15:
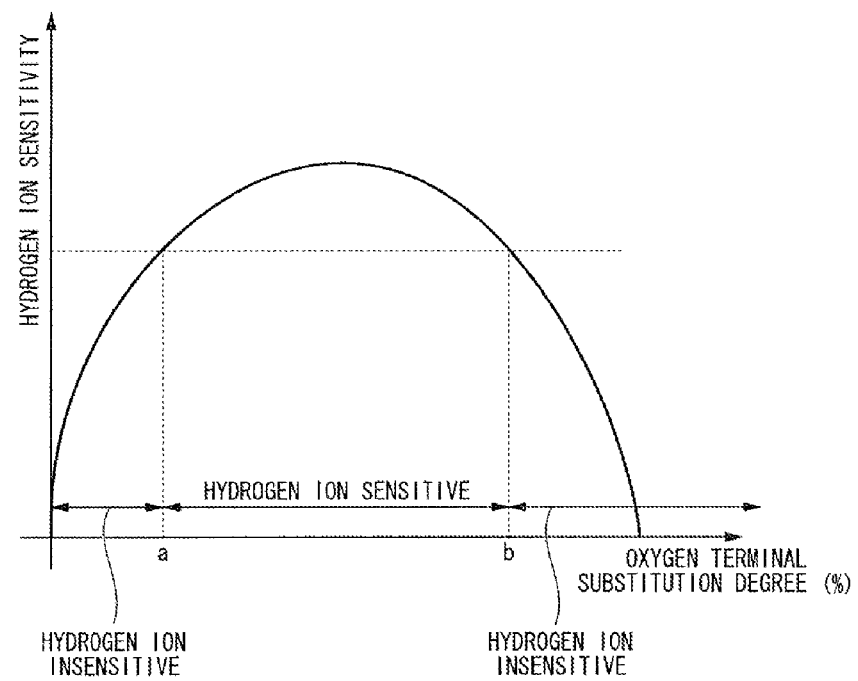
FIG. 15 is a characteristic diagram illustrating a relation between hydrogen ion sensitivity and an oxygen terminal substitution degree.

FIG. 15 is a characteristic diagram illustrating a relation between hydrogen ion sensitivity and an oxygen terminal substitution degree. The longitudinal axis shows the hydrogen ion sensitivity, and the transverse axis shows the oxygen terminal substitution degree. The oxygen terminal substitution degree used herein is expressed by the following formula:

Oxygen Terminal Substitution Degree=$A/(A+B)$ where A is the number of carbons on the diamond surface of the oxygen terminal, and B is the number of carbons on the diamond surface other than the oxygen terminal.

The oxygen terminal substitution degree of 0% refers to a diamond surface in which no oxygen terminal is present. The oxygen terminal substitution degree of 100% refers to a diamond surface in which only the oxygen terminal is present. For example, the oxygen terminal substitution degree of the hydrogen-terminated diamond has a value of approximately 0%.

As shown in FIG. 15, as the oxygen terminal substitution degree increases from 0%, the hydrogen ion sensitivity increases, and is eventually changed into reduction. When the oxygen terminal substitution degree exceeds a constant value, the hydrogen ion sensitivity is approximately zero. Accordingly, in the gate portion of the reference electrode, for example, the oxygen terminal substitution degree having a range within which the ion insensitivity of FIG. 15 can be obtained, i.e. a range equal to or less than a % or a range equal to or greater than b %, is selected. Further, in the gate portion of the working electrode, for example, the oxygen terminal substitution degree having a range within which the ion sensitivity of FIG. 15 can be obtained, i.e. a range of a % to b %, is selected.

According to the present invention as described above, in the ISFET of the terminal control diamond, in which the liquid electrolyte is adopted as the liquid to be measured and the gate is used as the reference electrode and the working electrode, it is possible to acquire a pH sensor having the reference electrode that is excellent in high-temperature and high-pressure, is acid and alkali resistant, and requires no internal liquid.

Thereby, it is possible to overcome the problem with leakage or time degradation of the internal liquid, which is the problem of the reference electrode of a type in which the internal liquid is contained. Further, it is possible to provide a pH sensor that enables accurate measurements in the bioprocess of processing bio-related materials such as proteins, for example, under strong-acid or -alkaline conditions of the semiconductor fabricating process of the chemical synthesis plant, and that contributes to visualization of a pH value in a production process.

As a type of the diamond used in the diamond ISFET of the present invention, signal crystal diamond may be used in addition to the exemplified polycrystalline diamond. Further, along with conductive diamond (doped diamond: polycrystal or single crystal), an elemental substance such as diamond-like carbon, conductive diamond-like carbon (doped diamond-like carbon), ECR sputtered carbon, RF sputtered carbon, carbon nanotube, fullerene, or carbon nanotube, and a conductive carbon material consisting essentially of one thereof may be used. Like the diamond, the ECR sputtered carbon, and the diamond-like carbon, a structure in which a ratio of a content of an sp$^3$ bonded crystal to a content of an sp$^2$ bonded crystal (an sp$^3$/sp$^2$ ratio) is mainly high is more preferable. Diamond having the highest fraction of the sp$^3$ bonded crystal is the most preferable in practicing the present invention.

When the conductive diamond thin film (doped diamond) is supported, mixed gas of hydrogen gas and carbon source is used as a diamond raw material in any method. To impart conductivity to the diamond, a trace of an element (dopant) whose valence is different from that of the diamond may be added. The dopant may include boron, phosphorus, or nitrogen, and may have a content of 1 to 100,000 ppm, preferably 100 to 10,000 ppm.

Figure 16:
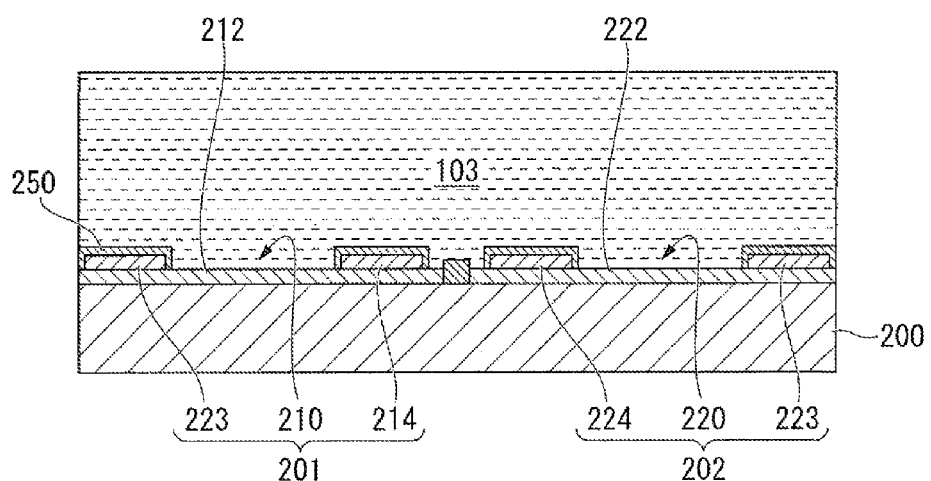
FIG. 16 is a cross-sectional view illustrating a pH sensor in accordance with a fifth preferred embodiment of the present invention.

FIG. 16 is a cross-sectional view illustrating a pH sensor in accordance with a fifth preferred embodiment of the present invention. In FIG. 16, a reference electrode and a working electrode are formed on a common substrate.

As shown in FIG. 16, a reference electrode 201 and a working electrode 202 are formed on a common silicon wafer 200. The reference electrode 201 and the working electrode 202 functionally correspond to the reference electrode 101 and the working electrode 102 shown in FIGS. 8 and 9, and pH can be measured on the same principle.

As shown in FIG. 16, the reference electrode 201 includes a diamond thin film 212 formed on a surface of the silicon wafer 200, a drain 213 formed on a surface of the diamond thin film 212, a source 214 formed on the surface of the diamond thin film 212 so as to be opposite to the drain 213, and a passivation layer 250 covering the drain 213 and the source 214. A region sandwiched between the drain 213 and the source 214 acts as a gate 210.

In a portion of the gate 210 of the reference electrode 201, the surface of the diamond thin film 212 is configured so that, when a concentration of hydrogen ions ranges from $1.0 \times 10^{-1}$ mol/L to $1.0 \times 10^{-14}$ mol/L, a terminal element is controlled so as to cause the potential to be stabilized, or to cause the uniformity of the potential to be maintained to such an extent that the ion sensitivity has no practical issue.

As shown in FIG. 16, the working electrode 202 includes a diamond thin film 222 formed on a surface of the silicon wafer 200, a drain 223 formed on a surface of the diamond thin film 222, and a source 224 formed on the surface of the diamond thin film 222 so as to be opposite to the drain 223. The drain 223 and the source 224 are covered by the passivation layer 250. A region sandwiched between the drain 223 and the source 224 acts as a gate 220.

The drain 223 and the source 224 may have the same shape as the drain 213 and the source 214 of the reference electrode 201.

In a portion of the gate 220 of the working electrode 202, the surface of the diamond thin film 222 is configured so that, when a concentration of hydrogen ions ranges from $1.0 \times 10^{-1}$ mol/L to $1.0 \times 10^{-14}$ mol/L, a terminal element is controlled so as to cause the potential to make a linear or non-linear response depending on pH value.

The control of the terminal element of the surface of each of the diamond thin films 212 and 222 can be carried out by an arbitrary process. For example, an as-grown diamond thin film is formed as the same layer constituting the diamond thin film 212 and the diamond thin film 222, and then each region is terminated, so that distribution of desired ion sensitivity can be obtained.

When pH is measured by the pH sensor shown in FIG. 16, a liquid 103 to be measured is in contact with the surface of the diamond thin film 212 within the region of the gate 210 sandwiched between the drain 213 and the source 214 of the reference electrode 201, as shown in FIG. 16. On the other hand, due to the presence of the passivation layer 250, the liquid 103 to be measured is not in direct contact with the drain 213 and the source 214.

Further, in the region of the gate 220 sandwiched between the drain 223 and the source 224 of the working electrode 202, the liquid 103 to be measured is in contact with the surface of the diamond thin film 222. On the other hand, due to the presence of the passivation layer 250, the liquid 103 to be measured is not in direct contact with the drain 223 and the source 224.

The pH of the liquid 103 to be measured is calculated based on a difference between operation characteristic and operation state of the reference electrode 201 and the working electrode 202, such as a difference in voltage-current characteristic between the drain and the source, or a difference in voltage of the gate of the reference electrode 201 and the working electrode 202 under constant conditions. For example, the circuit shown in FIG. 10 may be used.

Next, an example of compensating for a temperature of a diamond ISFET will be described with reference to FIGS. 17 and 18. To compensate for an influence on ion sensitivity caused by temperature, a temperature sensor may be installed.

The construction described below may be applied to either of the reference electrode and the working electrode.

Figure 17:
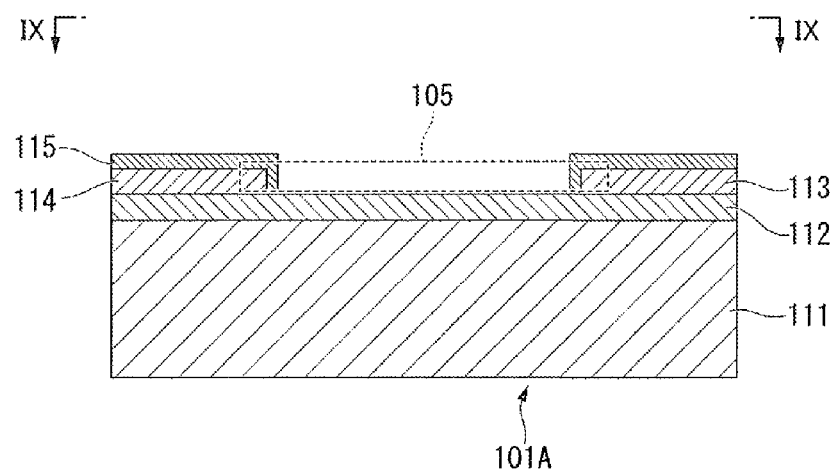
FIG. 17 is a cross-sectional view illustrating the construction of a reference electrode of a pH sensor in accordance with a sixth preferred embodiment of the present invention.

FIG. 17 is a cross-sectional view illustrating the construction of a reference electrode of a pH sensor in accordance with a sixth preferred embodiment of the present invention. The pH sensor in accordance with the sixth preferred embodiment of the present invention is provided with a thermistor 105.

Figure 18:
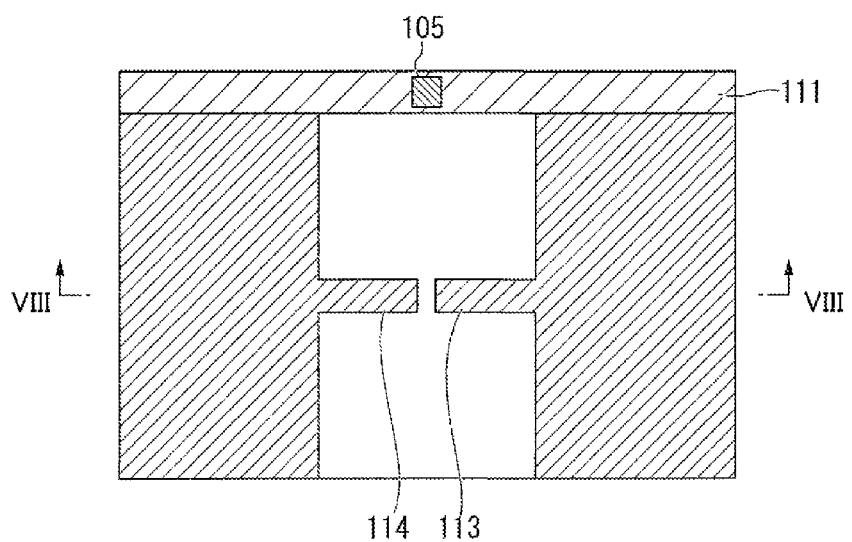
FIG. 18 is a plan view taken along a line IX-IX of the pH sensor in accordance with the sixth preferred embodiment of the present invention.

FIG. 18 is a plan view taken along a line IX-IX of FIG. 17. In FIGS. 17 and 18, the same elements as in FIGS. 8 and 9 are given the same numerals.

As shown in FIGS. 17 and 18, a thermistor 105 is formed as a temperature sensor on a silicon wafer 111 of a reference electrode 101A. A temperature characteristic of an ISFET constituting the reference electrode 101A is made up for based on a change in resistance value of the thermistor 105. In this case, it is possible to accurately measure pH at all times regardless of the temperature of the liquid to be measured. Similarly, such temperature compensation can also be performed on an output value of the working electrode based on the change of the resistance value of the thermistor 105.

As described above, according to the ion sensor of the present invention, since the reference electrode and the working electrode are formed as the p-channel FET, it is possible to overcome the problem with leakage or time degradation of the internal liquid in the reference electrode. Further, it is possible for the ion sensor to be applied to the bioprocess of processing bio-related materials such as proteins under strong-acid, or -alkaline conditions of the semiconductor fabricating process of the chemical synthesis plant.

The application of the present invention is not limited to the preferred embodiments above. The present invention may be widely applied to ion sensors, each of which includes a reference electrode and a working electrode, and measures the pH of a liquid to be measured based on outputs of the reference electrode and the working electrode.

As used herein, the following directional terms "forward, rearward, above, downward, vertical, horizontal, below, transverse, row and column" as well as any other similar directional terms refer to those directions of an apparatus equipped with the present invention. Accordingly, these terms, as utilized to describe the present invention should be interpreted relative to an apparatus equipped with the present invention.

The term "configured" is used to describe a component, unit or part of a device includes hardware and/or software that is constructed and/or programmed to carry out the desired function.

Moreover, terms that are expressed as "means-plus function" in the claims should include any structure that can be utilized to carry out the function of that part of the present invention.

The term "unit" is used to describe a component, unit or part of a hardware and/or software that is constructed and/or programmed to carry out the desired function. Typical examples of the hardware may include, but are not limited to, a device and a circuit.

While preferred embodiments of the present invention have been described and illustrated above, it should be understood that these are examples of the present invention and are not to be considered as limiting. Additions, omissions, substitutions, and other modifications can be made without departing from the scope of the present invention. Accordingly, the present invention is not to be considered as being limited by the foregoing description, and is only limited by the scope of the claims.

What is claimed is:

1. An ion sensor comprising:
  a reference electrode including a first p-channel field effect transistor (FET), the first p-channel FET including a first gate portion, a semiconductor surface of the first gate portion including hydrogen-terminated diamond; and a working electrode including a second p-channel FET, the second p-channel FET including a second gate portion, a semiconductor surface of the second gate portion including hydrogen-terminated diamond.

2. The ion sensor according to claim 1, wherein the semiconductor surface of the gate portion of the first p-channel FET includes hydrogen ion insensitive terminals in which an oxygen terminal or a fluorine terminal is substituted for part of hydrogen terminals of hydrogen-terminated diamond.

3. The ion sensor according to claim 1, wherein the semiconductor surface of the gate portion of the first p-channel FET has a content of an $sp^3$ bonded crystal which is more than a content of an $sp^2$ bonded crystal.

4. The ion sensor according to claim 1, wherein the semiconductor surface of the second gate portion includes ion sensitive terminals in which an amino terminal or an oxygen terminal is substituted for part of hydrogen terminals of hydrogen-terminated diamond.

5. The ion sensor according to claim 1, further comprising a temperature sensor that detects a temperature of at least one of the first and second p-channel FETs.

6. An ion concentration measurement method by using the ion sensor according to any one of claims 1 and 2-5, comprising:

a step of bringing a liquid to be measured into contact with the reference electrode and the working electrode; and a step of measuring an ion concentration of the liquid to be measured based on outputs of the reference electrode and the working electrode.

7. The ion sensor according to claim 1, wherein the reference electrode and the working electrode are formed on a common silicon wafer.

8. The ion sensor according to claim 1, wherein a terminal element in the semiconductor surface of the first gate portion is controlled to cause a potential of the semiconductor surface of the first gate portion to be stabilized when a concentration of hydrogen ions ranges from $1.0 \times 10^{-1}$ mol/L to $1.0 \times 10^{-14}$ mol/L.

9. The ion sensor according to claim 1, wherein a terminal element in the semiconductor surface of the second gate portion is controlled to cause a potential of the semiconductor surface of the second gate portion to make a linear or non-linear response depending on pH value when a concentration of hydrogen ions ranges from $1.0 \times 10^{-1}$ mol/L to $1.0 \times 10^{-14}$ mol/L.

* * * * *